US012383693B2

(12) United States Patent
LaTorraca et al.

(10) Patent No.: US 12,383,693 B2
(45) Date of Patent: Aug. 12, 2025

(54) VARIABLE THROAT JET VENTURI

(71) Applicant: HILL-ROM SERVICES PTE. LTD., Ot (SG)

(72) Inventors: Gary John LaTorraca, Batesville, IN (US); Tom Westfall, Batesville, IN (US)

(73) Assignee: HILL-ROM SERVICES PTE. LTD., Ot (SG)

( * ) Notice: Subject to any disclaimer, the term of this patent is extended or adjusted under 35 U.S.C. 154(b) by 867 days.

(21) Appl. No.: 17/563,380

(22) Filed: Dec. 28, 2021

(65) Prior Publication Data
US 2022/0249797 A1    Aug. 11, 2022

Related U.S. Application Data

(60) Provisional application No. 63/146,850, filed on Feb. 8, 2021.

(51) Int. Cl.
| | | |
|---|---|---|
| A61M 16/12 | (2006.01) | |
| A61M 16/00 | (2006.01) | |
| A61M 16/06 | (2006.01) | |
| A61M 16/08 | (2006.01) | |
| A61M 16/10 | (2006.01) | |

(Continued)

(52) U.S. Cl.
CPC ...... *A61M 16/127* (2014.02); *A61M 16/0666* (2013.01); *A61M 16/0883* (2014.02)

(58) Field of Classification Search
CPC .. A61M 16/127; A61M 16/20; A61M 16/205; A61M 16/0666–0677; A61M 39/228; A61M 16/0672; F04F 5/44; F04F 5/46; F04F 5/463; F04F 5/48; F04F 5/50; F04F 5/52
See application file for complete search history.

(56) References Cited

U.S. PATENT DOCUMENTS

| | | |
|---|---|---|
| 8,424,514 B2 | 4/2013 | Oates et al. |
| 9,132,250 B2 | 9/2015 | Allum et al. |

(Continued)

FOREIGN PATENT DOCUMENTS

| | | | |
|---|---|---|---|
| WO | WO9528193 | 10/1995 | |
| WO | WO-9528193 A1 * | 10/1995 | ............ A61M 16/00 |

OTHER PUBLICATIONS

Machine_Translation_WO_9528193_A1 (Year: 1995).*
European Search Report for EP 22 15 5155; mailed Jun. 27, 2022.

*Primary Examiner* — Kendra D Carter
*Assistant Examiner* — Mautin I Ashimiu
(74) *Attorney, Agent, or Firm* — Stetina Garred Brucker & Newboles

(57) ABSTRACT

A variable throat jet venturi for delivering ventilation gas to a patient includes a jet nozzle, a deformable throat body arranged to receive ventilation gas output by the jet nozzle and defining a gas inlet and a gas outlet, and a housing containing the deformable throat body. The housing may define an entrainment opening which is open to ambient air and a pilot pressure port for pressurizing a plenum between an outer wall of the deformable throat body and an inner wall of the housing. A pilot pressure line may be fluidly coupled to the pilot pressure port. A controller may be programmed to energize the pilot pressure line to constrict the deformable throat body during an exhalation phase of positive end-expiratory pressure (PEEP) therapy.

20 Claims, 5 Drawing Sheets

(51) Int. Cl.
*A61M 16/14* (2006.01)
*A61M 16/20* (2006.01)

(56) References Cited

U.S. PATENT DOCUMENTS

| | | | |
|---|---|---|---|
| 9,199,053 B1 | 12/2015 | Allum et al. | |
| 9,259,547 B2 | 2/2016 | Meynink et al. | |
| 9,370,635 B2 | 6/2016 | Ratner | |
| 10,384,028 B2 | 4/2019 | Allum et al. | |
| 10,293,132 B2 | 5/2019 | Martin | |
| 10,314,999 B1 | 6/2019 | Lei | |
| 10,576,241 B2 | 3/2020 | Volgyesi | |
| 10,709,864 B2 | 7/2020 | Kapust et al. | |
| 11,278,698 B2 | 3/2022 | Romano et al. | |
| 11,383,054 B2 | 7/2022 | Ratner | |
| 2003/0159696 A1* | 8/2003 | Boussignac | A61M 16/147 128/204.24 |
| 2010/0043796 A1* | 2/2010 | Meynink | A61M 16/208 128/205.24 |
| 2013/0190643 A1* | 7/2013 | Brambilla | A61M 16/206 128/205.25 |
| 2014/0020687 A1* | 1/2014 | Cullen | A61M 16/204 128/204.23 |
| 2019/0247595 A1 | 8/2019 | Pohlmann et al. | |
| 2020/0155783 A1 | 5/2020 | Allum et al. | |
| 2022/0296832 A1 | 9/2022 | Ratner | |

\* cited by examiner

1.1

1.2

2.1

2.2

3.1

3.2

4.1

4.2

VARIABLE THROAT JET VENTURI

CROSS-REFERENCE TO RELATED APPLICATIONS

The present application claims priority to U.S. Provisional Application Ser. No. 63/146,850 filed Feb. 8, 2021, the disclosure of which is incorporated herein by reference.

STATEMENT RE: FEDERALLY SPONSORED RESEARCH/DEVELOPMENT

Not Applicable

BACKGROUND

Non-invasive open ventilation (NIOV), in which the patient's airway remains open rather than being sealed by a mask, is of great advantage to patients with chronic obstructive pulmonary disease (COPD) and other respiratory conditions due to its minimal interference with activities of daily living. However, because the patient can freely exhale, there is no easy way to generate positive end-expiratory pressure (PEEP) for NIOV patients and doing so typically requires a high flow rate of gas to the patient, typically air and/or oxygen. The gas consumed generating PEEP is wasted, as is the energy to produce it. This results in larger, heavier devices and shorter battery run time. The required flow rate of gas can be reduced using pneumatic (e.g. poppet) valves or eliminated altogether using electrically operated valves. However, such valves are physically large, requiring the undesirable placement of a bulky element close to the patient's face, in addition to adding complexity and weight to the device and introducing dead space volume that increases carbon dioxide rebreathing.

BRIEF SUMMARY

The present disclosure contemplates various systems and methods for overcoming the above drawbacks accompanying the related art. One aspect of the embodiments of the present disclosure is a variable throat jet venturi for delivering ventilation gas to a patient. The variable throat jet venturi may comprise a jet nozzle, a deformable throat body arranged to receive ventilation gas output by the jet nozzle and defining a gas inlet and a gas outlet, and a housing containing the deformable throat body. The housing may define an entrainment opening which is open to ambient air and a pilot pressure port for pressurizing a plenum between an outer wall of the deformable throat body and an inner wall of the housing.

With the plenum in a first pressurization state, the variable throat jet venturi may achieve a shutoff pressure $P_{shutoff}$ at the gas outlet of at least 55 cmH$_2$O at a jet nozzle pressure $P_n$ of 10.5 psig and a jet nozzle flow $V'_n$ equal to or less than 30 slpm. With the plenum in a second pressurization state, the variable throat jet venturi may achieve a gas outlet pressure $P_{aw}$ of 10 cmH$_2$O at a jet nozzle flow $V'_n$ of less than 10 slpm, e.g. less than 5 slpm. With the plenum in the first pressurization state, a ratio $A_t/A_n$ of a cross-sectional area of the deformable throat body to a cross-sectional area of the jet nozzle may be between 20 and 30. With the plenum in the second pressurization state, the ratio $A_t/A_n$ may be between 2.0 and 5.0.

The deformable throat body may be arranged to receive the ventilation gas output by the jet nozzle through the entrainment opening of the housing.

Another aspect of the embodiments of the present disclosure is a patient ventilation interface. The patient ventilation interface may comprise the above variable throat jet venturi and a nasal coupler for fluidly coupling the gas outlet of the deformable throat body to a nostril of the patient. The nasal coupler may comprise a nasal pillow.

Another aspect of the embodiments of the present disclosure is a non-invasive ventilation system. The non-invasive ventilation system may comprise the above patient ventilation interface and a pilot pressure line fluidly coupled to the pilot pressure port. The non-invasive ventilation system may comprise a controller programmed to energize the pilot pressure line to constrict the deformable throat body during an exhalation phase of positive end-expiratory pressure (PEEP) therapy. The non-invasive ventilation system may comprise a multi-lumen tube having a ventilation gas lumen terminating in the nozzle and a pilot pressure lumen in fluid communication with the pilot pressure line.

Another aspect of the embodiments of the present disclosure is a method of varying a ratio between a throat diameter and a jet nozzle diameter of a variable throat jet venturi for delivering ventilation gas to a patient. The method may comprise providing a deformable throat body arranged to receive ventilation gas output by a jet nozzle and ambient air entrained via an entrainment opening, the deformable throat body defining a gas inlet and a gas outlet. The method may further comprise pressurizing a plenum between an outer wall of the throat body and an inner wall of a housing containing the deformable throat body to constrict the deformable throat body.

The pressurizing of the plenum may include energizing a pilot pressure line fluidly coupled to a pilot pressure port defined by the housing. The energizing of the pilot pressure line may be performed during an exhalation phase of positive end-expiratory pressure (PEEP) therapy.

The pressurizing of the plenum may comprise pressurizing the plenum from a first pressurization state, in which the variable throat jet venturi achieves a shutoff pressure $P_{shutoff}$ at the gas outlet of at least 55 cmH$_2$O at a jet nozzle pressure $P_n$ of 10.5 psig and a jet nozzle flow $V'_n$ equal to or less than 30 slpm, to a second pressurization state, in which the variable throat jet venturi achieves a gas outlet pressure $P_{aw}$ of 10 cmH$_2$O at a jet nozzle flow $V'_n$ of less than 10 slpm, e.g. less than 5 slpm. With the plenum in the first pressurization state, a ratio $A_t/A_n$ of a cross-sectional area of the deformable throat body to a cross-sectional area of the jet nozzle may be between 20 and 30. With the plenum in the second pressurization state, the ratio $A_t/A_n$ may be between 2.0 and 5.0.

Another aspect of the embodiments of the present disclosure is a variable throat jet venturi for delivering ventilation gas to a patient. The variable throat jet venturi may comprise a jet nozzle, a deformable throat body arranged to receive ventilation gas output by the jet nozzle and ambient air entrained via an entrainment opening and defining a gas inlet and a gas outlet, and a housing containing the deformable throat body. The housing may define a pilot pressure port for pressurizing a plenum between an outer wall of the deformable throat body and an inner wall of the housing.

With the plenum in a first pressurization state, the variable throat jet venturi may achieve a shutoff pressure $P_{shutoff}$ at the gas outlet of at least 55 cmH$_2$O at a jet nozzle pressure $P_n$ of 10.5 psig and a jet nozzle flow $V'_n$ equal to or less than 30 slpm. With the plenum in a second pressurization state, the variable throat jet venturi may achieve a gas outlet pressure $P_{aw}$ of 10 cmH$_2$O at a jet nozzle flow $V'_n$ of less than 10 slpm, e.g. less than 5 slpm. With the plenum in the first pressurization state, a ratio $A_t/A_n$ of a cross-sectional area of the deformable throat body to a cross-sectional area of the jet nozzle may be between 20 and 30. With the plenum in the second pressurization state, the ratio $A_t/A_n$ may be between 2.0 and 5.0.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

The present disclosure encompasses various embodiments of a variable throat jet venturi for delivering ventilation gas to a patient, along with systems and methods for varying a ratio between a throat diameter and a jet nozzle diameter thereof. The detailed description set forth below in connection with the appended drawings is intended as a description of several currently contemplated embodiments and is not intended to represent the only form in which the disclosed invention may be developed or utilized. The description sets forth the functions and features in connection with the illustrated embodiments. It is to be understood, however, that the same or equivalent functions may be accomplished by different embodiments that are also intended to be encompassed within the scope of the present disclosure. It is further understood that the use of relational terms such as first and second and the like are used solely to distinguish one from another entity without necessarily requiring or implying any actual such relationship or order between such entities.

Figure 1:
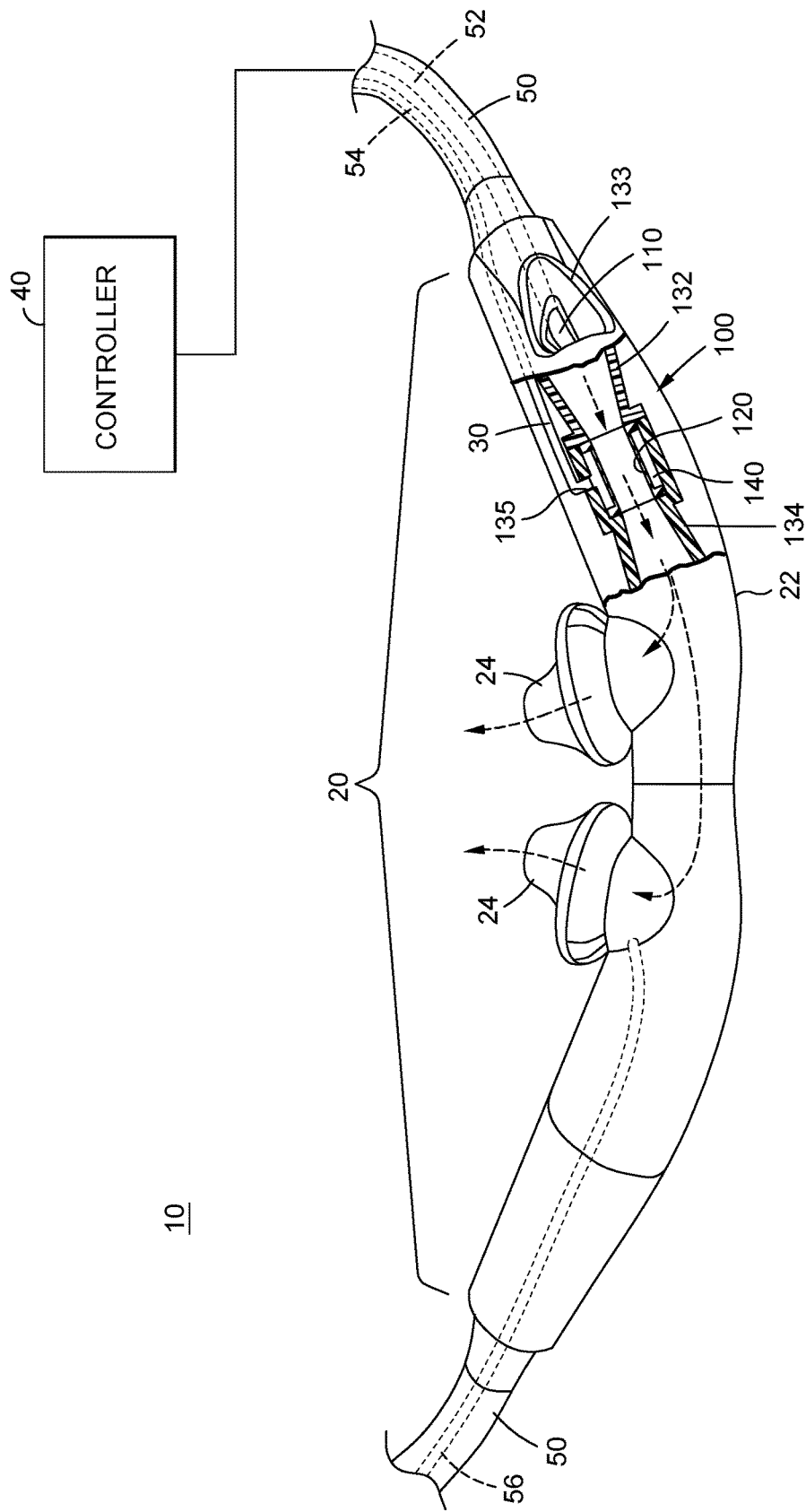
FIG. 1 shows an exemplary non-invasive ventilation system according to an embodiment of the present disclosure, with a variable throat jet venturi of the system shown in cutaway.

FIG. 1 shows an exemplary non-invasive ventilation system 10 according to an embodiment of the present disclosure, including a patient ventilation interface 20 that incorporates a variable throat jet venturi 100 for delivering ventilation gas to a patient. Due to the increased velocity of the ventilation gas at a constriction of the variable throat jet venturi 100, there is a decrease in pressure that causes ambient air to be entrained via one or more entrainment ports 133. By amplifying the ventilation gas output by a jet nozzle 110 in this way, the variable throat jet venturi 100 may serve as an efficient flow generator when providing ventilation therapy to the patient. Meanwhile, so that it may also serve as an efficient PEEP generator, the variable throat jet venturi 100 may include a deformable throat body 120 to serve as the constriction, with a housing 130 of the variable throat jet venturi 100 defining a pilot pressure port 135 for pressurizing a plenum 140 surrounding the deformable throat body 120 (e.g. via a feed and bleed circuit). By selectively pressurizing the plenum 140, the plenum 140 can be transitioned between a first pressurization state for maximizing airflow to the patient (e.g. during inhalation) and a second pressurization state in which the deformable throat body 120 is more constricted. In the latter state, the reduced cross-sectional area of the deformable throat body 120 may significantly reduce the required nozzle flow for achieving a desired output pressure, making it possible to efficiently generate PEEP.

As shown by way of example in FIG. 1, the patient ventilation interface 20 in which the variable throat jet venturi 100 is integrated may be a nasal interface having a pair of nasal couplers 24 (e.g. nasal pillows) for fluidly coupling a gas outlet of the deformable throat body 120 to the nostrils of the patient. Examples of such a nasal interface are described in U.S. Pat. No. 9,132,250, entitled METHODS, SYSTEMS AND DEVICES FOR NON-INVASIVE VENTILATION INCLUDING A NON-SEALING VENTILATION INTERFACE WITH AN ENTRAINMENT PORT AND/OR PRESSURE FEATURE, U.S. Pat. No. 9,675,774, entitled METHODS, SYSTEMS AND DEVICES FOR NON-INVASIVE OPEN VENTILATION WITH GAS DELIVERY NOZZLES IN FREE SPACE, U.S. Pat. No. 9,962,512, entitled METHODS, SYSTEMS AND DEVICES FOR NON-INVASIVE VENTILATION INCLUDING A NON-SEALING VENTILATION INTERFACE WITH A FREE SPACE NOZZLE FEATURE, and U.S. Pat. No. 10,792,449, entitled PATIENT INTERFACE WITH INTEGRATED JET PUMP, the entire contents of each of which are expressly incorporated by reference herein. For example, the variable throat jet venturi 100 may be disposed within or constitute a manifold assembly 22 of the patient ventilation interface 20, with the jet nozzle 110 integrated therewith or attachable to an end thereof. The manifold assembly 22 may be configured to fit between the patient's nose and upper lip and may serve to direct exit flow from the variable throat jet venturi 100 to the patient's nostrils.

With reference to FIG. 1, it is contemplated that the variable throat jet venturi 100 may be integrated in or otherwise provided at one side of the manifold assembly 22 only, with the exit flow thereof being directed simultaneously to both of the patient's nostrils as shown. Along these lines, as indicated above, the manifold assembly 22 of the patient ventilation interface 20 may be outfitted with the spaced, identically configured pair of the nasal couplers 24 (e.g. nasal pillows) engageable to and placeable into fluid communication with respective ones of the patient's nostrils, and the manifold assembly 22 may place the variable throat jet venturi 100 into fluid communication with both such nasal couplers 24 by a single flow passage. Alternatively, the manifold 22 may define separate flow passages for each of the patient's left and right nostrils, in which case the variable throat jet venturi 100 and some or all of its features described herein may be duplicated for each side of the manifold 22.

In order to provide for the pressurization of the plenum 140 as described above, the non-invasive ventilation system 10 may include a pilot pressure line 30 fluidly coupled to the pilot pressure port 135. A controller 40 may be programmed to energize the pilot pressure line 30 to constrict the deformable throat body 120 during an exhalation phase of PEEP therapy. In the illustrated example, the non-invasive ventilation system 10 includes a multi-lumen tube 50 having a ventilation gas lumen 52 terminating in the jet nozzle 110 and a pilot pressure lumen 54 in fluid communication with the pilot pressure line 30. The ventilation gas lumen 52 may receive ventilation gas from a ventilator or an oxygen concentrator, for example. The pilot pressure line 30 may extend from the multi-lumen tube 50 forward past the jet nozzle 110 to the pilot pressure port 135 of the variable throat jet venturi 100.

Additional lumens of the multi-lumen tube 50 may include, for example, a low-pressure gas lumen for oxygen (which may terminate in a low-pressure jet nozzle outlet port near the jet nozzle 110), a pressure sensing lumen (which may extend farther downstream to terminate nearer to the patient's nostril, such as at the base of the nasal coupler 24 closest the variable throat jet venturi 100, for example), lumens for medicaments, etc. However, it is contemplated that in a preferred implementation, a second tube 50 may be provided which routes one or more of these lumens to the other side of the manifold assembly 22 (i.e., the side opposite that having the variable throat jet venturi 100 integrated therein). Such a pair of tubes 50 may branch upstream from a single multi-lumen tube using a wye connector such as that described in U.S. Pat. No. 10,792,449, incorporated by reference above. In FIG. 1, for example, a second tube 50 is shown having, as its only lumen, a pressure sensing lumen 56 that extends to the base of one of the nasal couplers 24 in order to desirably measure pressure downstream of the variable throat jet venturi 100. In this example, the first tube 50 will have no pressure sensing lumen. Along these lines, it is contemplated that any of the above-described lumens may be provided individually or in some prescribed combination at one or both sides of the interface 20 using the first tube 50 with or without the second tube 50.

In a case where the non-invasive ventilation system 10 may include only a single multi-lumen tube 50 extending to the patient ventilation interface 20, it is also contemplated that the multi-lumen tube 50 may interface with the manifold 22 at a central position equidistant from the nasal couplers 24. For example, the multi-lumen tube 50 may connect to the manifold 22 between the nasal couplers 24 on the bottom or the front of the manifold 22 as viewed in FIG. 1. In such case, this same central area, near the bases of the nasal couplers 24, may house a single variable throat jet venturi 100 that is fed by the multi-lumen tube 50 and whose output flow is directed simultaneously to both nasal couplers 24. As another possibility, the disclosed variable throat jet venturi 100 may be embodied in a detachable connector that interfaces the multi-lumen tube 50 with a mask or other patient interface at any appropriate position (and in some cases may be universally usable with multiple different patient interfaces). Examples of such connectors that can be equipped with the disclosed variable throat jet venturi 100 are the adaptors disclosed in U.S. Pat. No. 10,307,552, entitled JET PUMP ADAPTOR FOR VENTILATION SYSTEM, the entire contents of which are expressly incorporated by reference herein.

The controller 40 may be a standalone device dedicated to energizing the pilot pressure line 30 during PEEP therapy (e.g. based on sensor input indicative of an exhalation phase of a patient's breathing) or may be a controller of a ventilator or oxygen concentrator, for example. In this regard, exemplary ventilators and oxygen concentrators that may be used with the disclosed embodiments include, in addition to those incorporated by reference above, those described in U.S. Pat. No. 10,369,320, entitled MODULAR VENTILATION SYSTEM, U.S. Patent Application Pub. No. 2019/0307981, entitled MODULAR VENTILATION SYSTEM, and U.S. patent application Ser. No. 16/874,472, filed May 14, 2020 and entitled O2 CONCENTRATOR WITH SIEVE BED BYPASS AND CONTROL METHOD THEREOF," the entire contents of each of which are expressly incorporated herein by reference. The controller 40 may energize the pilot pressure line 30 by controlling the pressure in the pilot pressure lumen 54 of the multi-lumen tube 50, for example, by controlling a valve of a pilot pressure output port of a ventilator, oxygen concentrator, or other gas source that houses or is connected to the controller 40.

Figure 2A:
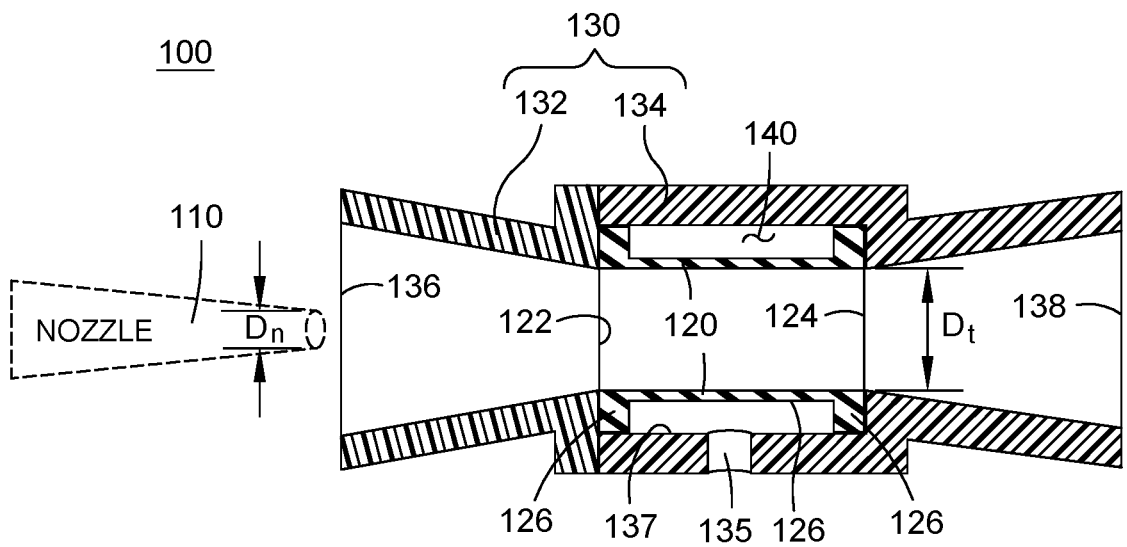
FIG. 2A is a cross-sectional view of the variable throat jet venturi with a plenum thereof in a first pressurization state.
Figure 2B:
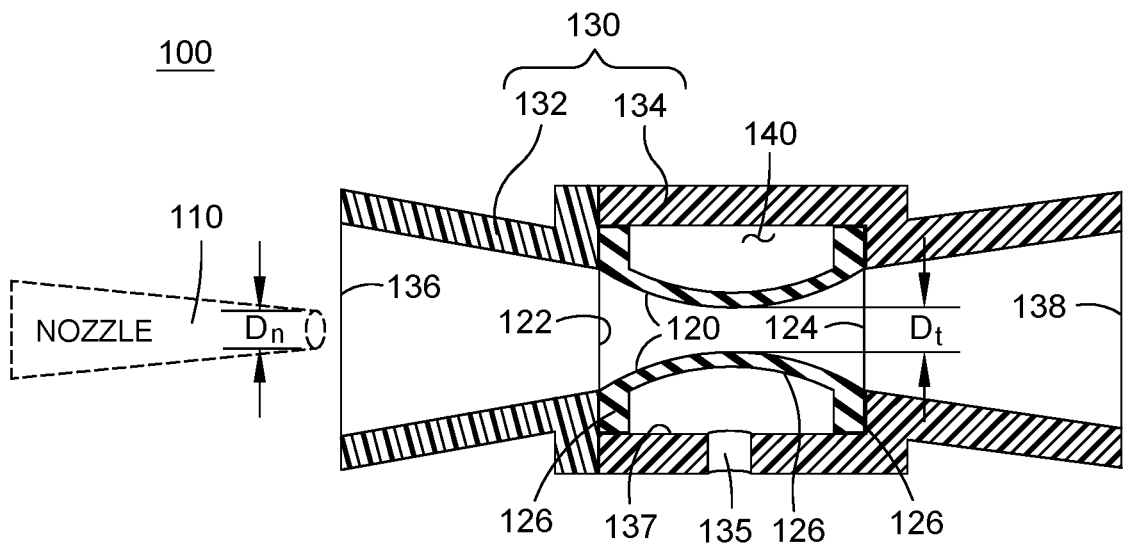
FIG. 2B is a cross-sectional view of the variable throat jet venturi with the plenum in a second pressurization state.
Figure 3A:
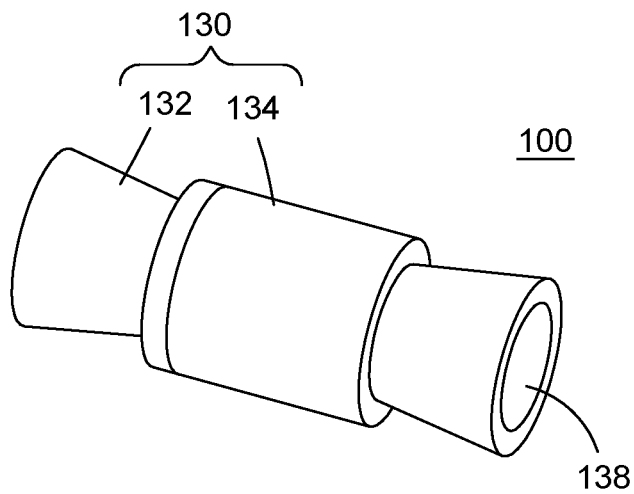
FIG. 3A is a perspective view of the variable throat jet venturi.
Figure 3B:
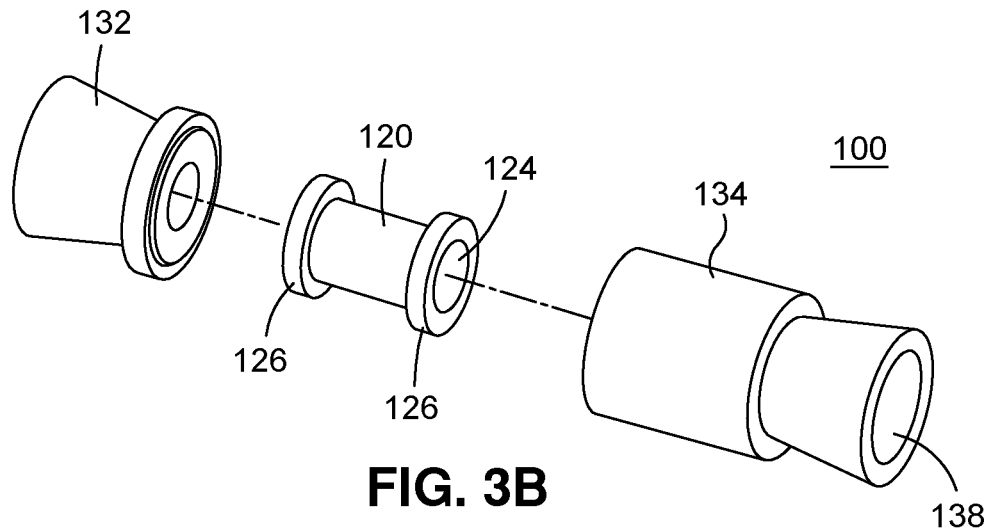
FIG. 3B is an exploded view of the variable throat jet venturi.
Figure 3C:
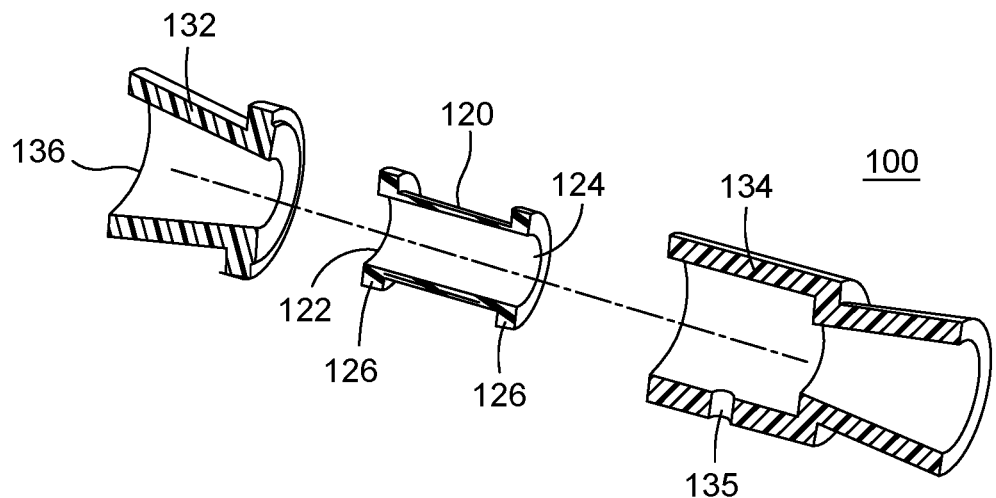
FIG. 3C is an exploded sectional view of the variable throat jet venturi.

FIGS. 2A and 2B are cross-sectional views of the variable throat jet venturi 100 with the plenum 140 in the first pressurization state and the second pressurization state, respectively. FIGS. 3A-3C are additional perspective, exploded and exploded sectional views of the variable throat jet venturi 100. As can be seen in FIGS. 2A and 2B, when pressure increases in the plenum 140 (e.g. by activation of a pilot pressure line 30, see FIG. 1), the plenum 140 transitions from the first pressurization state (FIG. 2A) to the second pressurization state (FIG. 2B), with the buildup of pressure in the plenum 140 causing the deformable throat body 120 to become constricted. More specifically, a cross-sectional area $A_t$ of the deformable throat body 120 (e.g. a smallest cross-sectional area corresponding to a diameter $D_t$ in FIGS. 2A and 2B) decreases from the first pressurization state to the second pressurization state. Given a nozzle having a fixed cross-sectional area $A_n$ (corresponding to a diameter $D_n$), the ratio $A_t/A_n$ thus decreases, reducing the required nozzle flow for achieving PEEP.

The deformable throat body 120 may define a gas inlet 122 and a gas outlet 124 and may have a generally tubular shape in its relaxed (e.g. as-molded) state as best shown in FIG. 3B. Flanges 126 may be defined at either end. Referring back to FIGS. 2A and 2B, when the deformable throat body 120 is disposed within the housing 130, the flanges 126 may function to position the deformable throat body 120 in a cavity defined therein. The flanges 126 may also serve to delineate a longitudinal extent of the plenum 140 between an outer wall 126 of the deformable throat body 120 and an inner wall 137 of the housing 130. As the plenum 140 is pressurized as shown in FIG. 2B, the pressure may cause the deformable throat body 120 to constrict about its center while the flanges 126 remain firmly against the inner wall 137 of the housing 130 (with or without the use of adhesive). Thereafter, as the plenum 140 is depressurized, the deformable throat body 120 may return to its relaxed state as shown in FIG. 2A. The deformable throat body 120 may be a thermoplastic elastomer (TPE) or a thermoset produced by liquid injection molding (LIM) using liquid silicone rubber (LSR), for example.

The housing 130 may be assembled from one or more pieces 132, 134 as shown, which may be attached to each other by ultrasonic welding, for example. The pieces 132, 134 of the housing 130 may similarly be made of a thermoplastic or thermoset but may typically (but not necessarily) have greater rigidity than the deformable throat body 120. In the illustrated example, there is an entry piece 132 and an exit piece 134. In more detail, as shown in FIGS. 2A-3C, the entry piece 132 of the housing 130 includes a generally frustoconical portion which flares outwardly away from the plenum 140 and defines an entrainment opening 136 open to ambient air. The exit piece 134 includes the inner wall 137 that defines the plenum 140, and likewise includes a generally frustoconical portion which flares outwardly away from the plenum 140 and serves as a diffuser 138 that may provide the desired airflow and/or pressure to the patient, e.g. via the nasal couplers 24 (see FIG. 1). With the arrangement shown in FIG. 1, the deformable throat body 120 may receive the ventilation gas output by the jet nozzle 110 via the entrainment opening 136 of the housing 130, in addition to ambient air which is drawn through the entrainment port 133 of the manifold assembly 22 and likewise introduced into the entrainment opening 136. In this regard, as seen in FIG. 1, the entrainment opening 136 (and hence the deformable throat body 120) fluidly communicates with both the jet nozzle 110 and entrainment port 133 of the manifold assembly 22. The distal tip of the jet nozzle 110 may be either outside the entrainment opening 136 as shown or inside the entry piece 132 downstream of the entrainment opening 136, closer to the gas inlet 122 of the deformable throat body 120, with the entrainment of ambient air occurring around the periphery of the jet nozzle 110 in either case.

In the implementation shown in FIG. 1 wherein the manifold assembly 22 includes the entrainment port 133 and the distal tip of the jet nozzle 110 is radially aligned with a portion of the entrainment port 133, it is contemplated that the entrainment opening 136 may likewise be radially aligned with a portion of the entrainment port 133, or located downstream therefrom. The same relative positioning options between the entrainment opening 136 and the entrainment port 133 are available if the distal tip of the jet nozzle 110 is disposed inside the entry piece 132 downstream of the entrainment opening 136. While the entrainment port 133 is depicted in FIG. 1 as being formed in the manifold assembly 22, it may alternatively be formed in a detachable nozzle assembly which contains the jet nozzle 110 and is rigidly or rotatably engaged to a corresponding end of an alternatively configured manifold assembly devoid of the entrainment port 133. Along these lines, variants of the patient ventilation interface 20 shown in FIG. 1 are also contemplated wherein the entrainment opening 136 of the variable throat jet venturi 100 may be arranged to draw ambient air directly therein, as opposed to ambient air being channeled thereto from a separate entrainment port or opening such as the entrainment port 133. In this instance, ambient air drawn directly into the entrainment opening 136 may flow about the periphery of the jet nozzle 110, particularly if the distal tip thereof resides within the entry piece 132 downstream of the entrainment opening 136. In any case, however, the deformable throat body 120 is arranged to receive, at its gas inlet 122, the ventilation gas output by the jet nozzle 110 together with ambient air entrained into entrainment opening 136 either directly or after passing through the entrainment port 133.

The geometry of the variable throat jet venturi 100, including the cross-sectional area of the nozzle 110 and in particular the geometry of the deformable throat body 120 when the plenum 140 is in the first and second pressurization states, may be selected to achieve desired performance characteristics. For purposes of illustration, maximum ventilator output capabilities may dictate a nozzle flow $V'_n \leq 30$ slpm and a nozzle pressure $P_n = 10.5$ psig, which, in turn, may limit the range of possible nozzle diameters. Using each of a plurality of possible nozzle diameters, candidate venturi geometries may be tested with the deformable throat body 120 in the relaxed state (plenum 140 in the first pressurization state as shown in FIG. 2A) to determine a shutoff pressure $P_{shutoff}$ at the gas outlet 124 of the deformable throat body 120 and a maximum output flow $V'_{aw-max}$ at the maximum nozzle pressure $P_n = 10.5$. In this way, it can be confirmed whether the candidate venturi geometry meets desired $P_{shutoff}$-$V'_{aw-max}$ performance. The same candidate venturi geometries may then be tested with the deformable throat body 120 in the constricted state (plenum 140 in the second pressurization state as shown in FIG. 2B) to determine the nozzle flow $V'_n$ needed to achieve PEEP, e.g. $P'_{aw} = 10$ cmH$_2$O, and the maximum output flow $V'_{aw-max}$ at that same nozzle flow $V'_n$.

Figure 4:
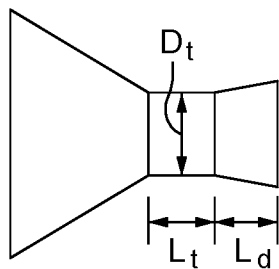
FIG. 4 shows four exemplary candidate venturi geometries in relaxed and constricted states corresponding to first and second plenum pressurization states.
Figure 4:
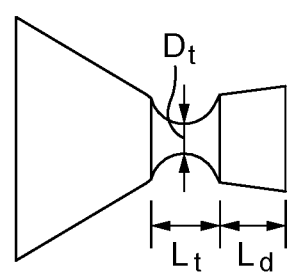
Figure 4:
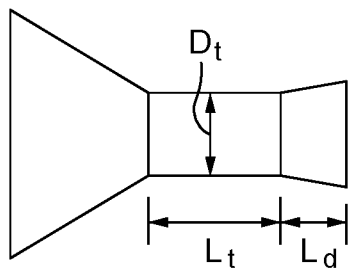
Figure 4:
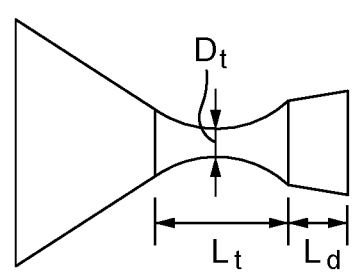
Figure 4:
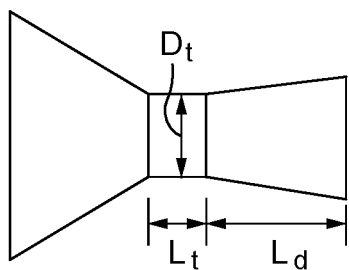
Figure 4:
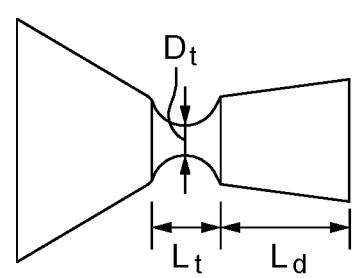
Figure 4:
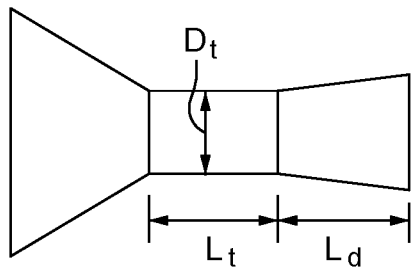
Figure 4:
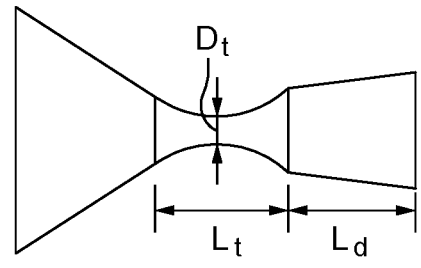

Exemplary data illustrating results of such a testing procedure is shown below in Tables 1 and 2, for a first nozzle 110 having a nozzle diameter $D_n = 0.043$ inches (cross-sectional area $A_n = 0.0015$ in$^2$) and a second nozzle 110 having a nozzle diameter $D_n = 0.048$ inches (cross-sectional area $A_n = 0.0018$ in$^2$), respectively. In Tables 1 and 2, the test numbers "#" are in the form "x.y" where x denotes different candidate venturi geometries 1, 2, 3, and 4 and y denotes relaxed ("1") and constricted ("2") states of the deformable throat body 120 thereof, as depicted in FIG. 4. The venturi geometries themselves are defined by a minimum cross-sectional diameter $D_t$ (and minimum cross-sectional area $A_t$) of the deformable throat body 120, a length $L_t$ from the gas inlet 122 to the gas outlet 124 of the deformable throat body 120, and a length $L_d$ from the gas outlet 124 to the end of the diffuser 138. In the example data of Tables 1 and 2, the deformable throat body 120 is assumed to receive the ventilation gas output by the jet nozzle 110 through the entrainment opening 136 of the housing 130 as shown in FIGS. 2A and 2B, with the length between the nozzle 110 and the gas inlet 122 of the deformable throat body 120 being 0.4 inches.

TABLE 1

| # | $D_t$ (in) | $A_t/A_n$ | $L_t$ (in) | $L_d$ (in) | $L_t + L_d$ (in) | $P_n$ (psig) | $V'_n$ (slpm) | $P_{shutoff}$ (cmH$_2$O) | $P_{aw}$ (cmH$_2$O) | $V'_{aw}$ (slpm) |
|---|---|---|---|---|---|---|---|---|---|---|
| 1.1 | 0.25 | 34 | 0.20 | 0.20 | 0.40 | 2.8 | 9.4 | 10.0 | 0.0 | 40.8 |
| | | | | | | 10.5 | 19.6 | 35.0 | 2.0 | 80.9 |
| 2.1 | 0.25 | 34 | 0.40 | 0.20 | 0.60 | 2.6 | 9.6 | 10.0 | 0.0 | 45.2 |
| | | | | | | 10.5 | 19.5 | 39.0 | 3.0 | 89.0 |
| 3.1 | 0.25 | 34 | 0.20 | 0.40 | 0.60 | 2.8 | 10.2 | 10.0 | 0.0 | 43.6 |
| | | | | | | 10.5 | 19.9 | 36.0 | 2.5 | 86.8 |
| 4.1 | 0.25 | 34 | 0.40 | 0.40 | 0.80 | 2.6 | 9.5 | 10.0 | 0.0 | 48.0 |
| | | | | | | 10.5 | 19.4 | 39.0 | 3.5 | 95.8 |
| 1.2 | 0.086 | 4 | 0.20 | 0.20 | 0.40 | 0.5 | 3.9 | 10.0 | 0.0 | 7.0 |
| | | | | | | 10.5 | 20.9 | 150.0 | 0.0 | 30.8 |
| 2.2 | 0.086 | 4 | 0.40 | 0.20 | 0.60 | 0.6 | 4.1 | 10.0 | 0.0 | 6.7 |
| | | | | | | 10.5 | 20.1 | 145.0 | 0.0 | 27.7 |
| 3.2 | 0.086 | 4 | 0.20 | 0.40 | 0.60 | 0.5 | 3.8 | 10.0 | 0.0 | 6.5 |
| | | | | | | 10.5 | 19.6 | 150.0 | 0.0 | 28.6 |
| 4.2 | 0.086 | 4 | 0.40 | 0.40 | 0.80 | 0.5 | 4.5 | 10.0 | 0.0 | 6.8 |
| | | | | | | 10.5 | 24.1 | 150.0 | 0.0 | 31.6 |

TABLE 2

| # | $D_t$ (in) | $A_t/A_n$ | $L_t$ (in) | $L_d$ (in) | $L_t + L_d$ (in) | $P_n$ (psig) | $V'_n$ (slpm) | $P_{shutoff}$ (cmH$_2$O) | $P_{aw}$ (cmH$_2$O) | $V'_{aw}$ (slpm) |
|---|---|---|---|---|---|---|---|---|---|---|
| 1.1 | 0.25 | 27 | 0.20 | 0.20 | 0.40 | 2.6 | 12.4 | 10.0 | 0.0 | 36.6 |
|  |  |  |  |  |  | 10.5 | 28.1 | 40.0 | 2.0 | 75.8 |
| 2.1 | 0.25 | 27 | 0.40 | 0.20 | 0.60 | 2.2 | 10.9 | 10.0 | 0.0 | 36.0 |
|  |  |  |  |  |  | 10.5 | 28.9 | 47.5 | 2.5 | 83.0 |
| 3.1 | 0.25 | 27 | 0.20 | 0.40 | 0.60 | 2.5 | 11.3 | 10.0 | 0.0 | 31.0 |
|  |  |  |  |  |  | 10.5 | 27.8 | 41.0 | 2.0 | 73.6 |
| 4.1 | 0.25 | 27 | 0.40 | 0.40 | 0.80 | 2.2 | 10.3 | 10.0 | 0.0 | 35.4 |
|  |  |  |  |  |  | 10.5 | 28.2 | 47.0 | 3.0 | 85.0 |
| 1.2 | 0.086 | 3 | 0.20 | 0.20 | 0.40 | 0.5 | 4.1 | 10.0 | 0.0 | 6.7 |
|  |  |  |  |  |  | 10.5 | 28.3 | 150.0 | 0.0 | 32.7 |
| 2.2 | 0.086 | 3 | 0.40 | 0.20 | 0.60 | 0.5 | 4.5 | 10.0 | 0.0 | 6.6 |
|  |  |  |  |  |  | 10.5 | 27.7 | 150.0 | 0.0 | 32.0 |
| 3.2 | 0.086 | 3 | 0.20 | 0.40 | 0.60 | 0.5 | 4.3 | 10.0 | 0.0 | 6.3 |
|  |  |  |  |  |  | 10.5 | 25.7 | 150.0 | 0.0 | 32.0 |
| 4.2 | 0.086 | 3 | 0.40 | 0.40 | 0.80 | 0.4 | 4.3 | 10.0 | 0.0 | 6.9 |
|  |  |  |  |  |  | 10.5 | 25.8 | 150.0 | 0.0 | 33.9 |

An exemplary test procedure for generating data like that of Tables 1 and 2 may be as follows for each test number "#". First, the gas outlet 124 (or the end of the diffuser 138) is occluded and the nozzle flow $V'_n$ is increased until the outlet pressure $P_{aw}$ is equal to the target PEEP, e.g. $P_{shutoff}$=10 cmH2O. The nozzle flow $V'_n$ and nozzle pressure $P_n$ are recorded in the first row. The gas outlet 124 is then opened and the outlet pressure $P_{aw}$ and output flow $V'_{aw}$ are recorded in the same row. Next, the nozzle pressure $P_n$ is set to the target maximum 10.5 psig. The nozzle flow $V'_n$, outlet pressure $P'_{aw}$, and output flow $V'_{aw}$ are now recorded in the second row. Lastly, the gas outlet 124 is again occluded, and the shutoff pressure $P_{shutoff}$ corresponding to the maximum nozzle flow $V'_n$ is recorded in the second row. The procedure can be repeated for different nozzles and candidate venturi geometries with the deformable throat body 120 in both relaxed and constricted states (corresponding to the first and second states of the plenum 140 shown in FIGS. 2A and 2B).

To calculate the maximum output flow $V'_{aw\text{-}max}$, the measured output flow $V'_{aw}$ taken at the target maximum nozzle pressure $P_n$ of 10.5 psig can be multiplied by the corresponding shutoff pressure $P_{shutoff}$ and divided by the difference between the shutoff pressure $P_{shutoff}$ and the corresponding measured outlet pressure $P'_n$, as follows: $V'_{aw\text{-}max} = V'_{aw} * P_{shutoff}/(P_{shutoff} - P_{aw})$. The ratio $X_{max}$ of the maximum output flow $V'_{aw\text{-}max}$ to the maximum nozzle flow $V'_n$ can be calculated as follows: $X_{max} = V'_{aw\text{-}max}/V'_n$.

The performance characteristics of interest can then be tabulated from the combined data of the relaxed and constricted states of the deformable throat body 120 of each candidate venturi geometry, as summarized in Tables 3 and 4 below for nozzle diameters $D_n$=0.043 inches and $D_n$=0.048 inches, respectively:

TABLE 3

| | RELAXED | | | | CONSTRICTED |
|---|---|---|---|---|---|
| # | $V'_n$ at $P_n$ = 10.5 psig | $P_{shutoff}$ at $P_n$ = 10.5 psig | $V'_{aw\text{-}max}$ at $P_n$ = 10.5 psig | $X_{max}$ | $V'_n$ at PEEP = 10 mm H$_2$O |
| 1 | 19.6 | 35.0 | 85.8 | 4.4 | 3.9 |
| 2 | 19.5 | 39.0 | 96.4 | 4.9 | 4.1 |
| 3 | 19.9 | 36.0 | 93.3 | 4.7 | 3.8 |
| 4 | 19.4 | 39.0 | 105.2 | 5.4 | 4.5 |

TABLE 4

| | RELAXED | | | | CONSTRICTED |
|---|---|---|---|---|---|
| # | $V'_n$ at $P_n$ = 10.5 psig | $P_{shutoff}$ at $P_n$ = 10.5 psig | $V'_{aw\text{-}max}$ at $P_n$ = 10.5 psig | $X_{max}$ | $V'_n$ at PEEP = 10 mm H$_2$O |
| 1 | 28.1 | 40.0 | 79.8 | 2.8 | 4.1 |
| 2 | 28.9 | 47.5 | 87.6 | 3.0 | 4.5 |
| 3 | 27.8 | 41.0 | 77.4 | 2.8 | 4.3 |
| 4 | 28.2 | 47.0 | 90.8 | 3.2 | 4.3 |

An exemplary venturi geometry that achieves desired performance characteristics is shown in Table 5, below, with unused data omitted, for a nozzle 110 having a nozzle diameter $D_n$=0.048 inches (cross-sectional area $A_n$=0.0018 in$^2$). Again, the deformable throat body 120 is assumed to receive the ventilation gas output by the jet nozzle 110 through the entrainment opening 136 of the housing 130 as shown in FIGS. 2A and 2B, with the length between the nozzle 110 and the gas inlet 122 of the deformable throat body 120 being 0.4 inches.

TABLE 5

| # | $D_t$ (in) | $A_t/A_n$ | $L_t$ (in) | $L_d$ (in) | $L_t + L_d$ (in) | $P_n$ (psig) | $V'_n$ (slpm) | $P_{shutoff}$ (cmH$_2$O) | $P_{aw}$ (cmH$_2$O) | $V'_{aw}$ (slpm) |
|---|---|---|---|---|---|---|---|---|---|---|
| 5.1 | 0.23 | 23 | 0.40 | 0.40 | 0.80 | — | — | 10.0 | — | — |
|  |  |  |  |  |  | 10.5 | 24.3 | 57.0 | 3.0 | 91.0 |
| 5.2 | 0.086 | 3 | 0.40 | 0.40 | 0.80 | 0.4 | 4.3 | 10.0 | 0.0 | — |
|  |  |  |  |  |  | 10.5 | — | — | — | — |

The tabulated performance characteristics of interest from the combined data of the relaxed and constricted states of the deformable throat body 120 of the above candidate venturi geometry #5 are summarized in Table 6 below:

TABLE 6

| # | RELAXED | | | | CONSTRICTED |
|---|---|---|---|---|---|
| | $V'_n$ at $P_n$ = 10.5 psig | $P_{shutoff}$ at $P_n$ = 10.5 psig | $V'_{aw-max}$ at $P_n$ = 10.5 psig | $X_{max}$ | $V'_n$ at PEEP = 10 mm $H_2O$ |
| 5 | 24.3 | 57.0 | 96.1 | 4.0 | 4.3 |

Figure 5:
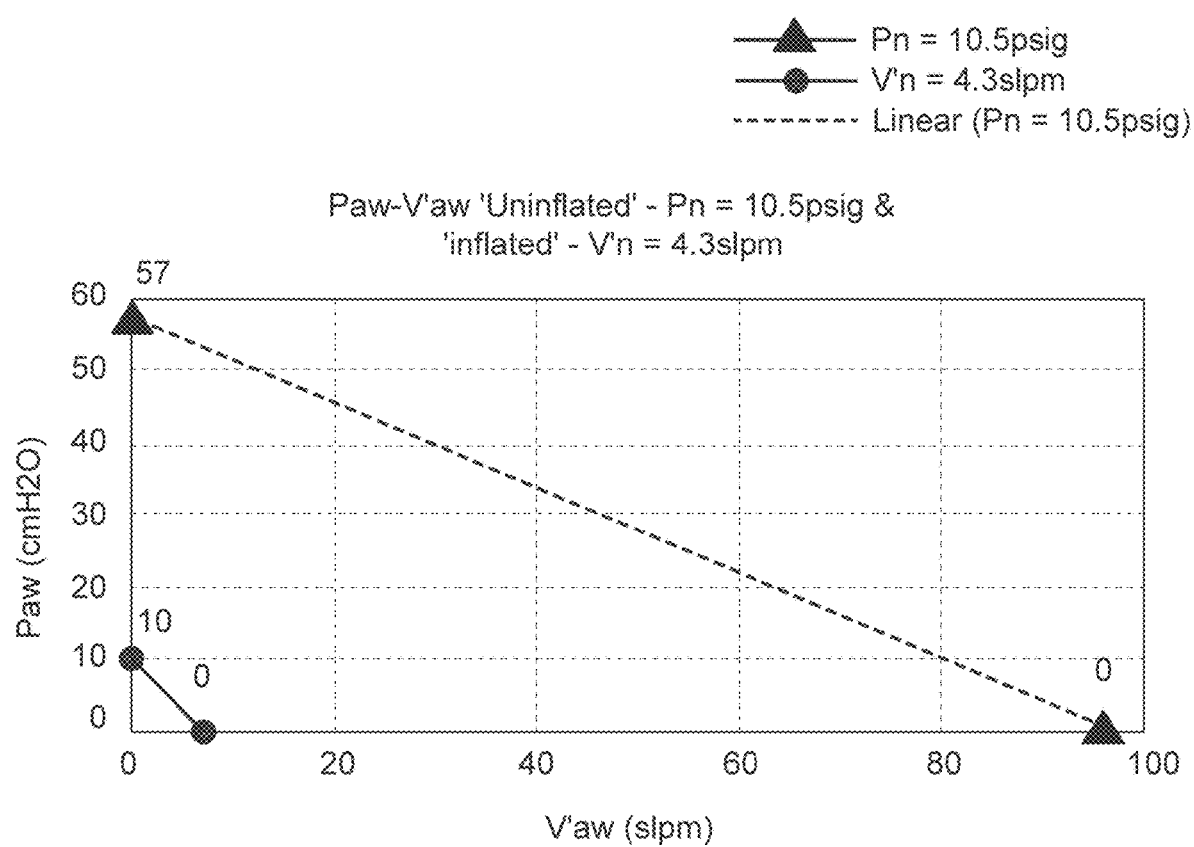
FIG. 5 graphically depicts performance characteristics of an exemplary variable throat jet venturi.

As can be seen from Tables 5 and 6 (and as graphically depicted in FIG. 5), a variable throat jet venturi 100 having a candidate venturi geometry #5 achieves a shutoff pressure $P_{shutoff}$ at the gas outlet 124 of 57.0 $cmH_2O$ (meeting target performance characteristics of at least 55 $cmH_2O$) at a jet nozzle pressure $P_n$ of 10.5 psig and a jet nozzle flow $V'_n$ of 24.3 lpm (which is less than or equal to 30 slpm) while the plenum 140 is in a first pressurization state (uninflated) corresponding to the relaxed state of the deformable throat body 120. A maximum output flow $V'_{aw-max}$=96.1 is achieved. Meanwhile, when the plenum 140 is in a second pressurization state (inflated) corresponding to the constricted state of the deformable throat body 120, the same variable throat jet venturi 100 achieves PEEP (gas outlet pressure $P_{aw}$=10 cmH2O) at a jet nozzle flow $V'_n$ of 4.3 slpm. Thus, using a variable throat jet venturi 100 having a deformable throat body 120 as described herein, PEEP (e.g. gas outlet pressure $P_{aw}$=10 cmH2O) can be achieved at a jet nozzle flow $V'_n$ of less than 10 slpm, which is less than half of the 20 slpm that is typically required with conventional NIOV devices and, in some cases, at a jet nozzle flow $V'_n$ of less than 5 slpm, which is less than a quarter of typical requirements. It is worth noting, however, that energizing a pilot pressure line 30 as used in some implementations of the disclosed deformable throat body 120 may use some airflow, e.g. 1 slpm.

Equivalent testing can be performed to select a venturi geometry that meets design constraints of any patient interface 20, for example, one in which one or more entrainment openings 136 have a side-by-side relationship with the jet nozzle 110 and/or for different lengths between the nozzle 110 and the gas inlet 122 of the deformable throat body 120. Along the same lines, the venturi geometry can be selected to meet different performance characteristics, including different maximum ventilator output capabilities other than nozzle flow $V'_n \leq 30$ slpm and nozzle pressure $P_n$=10.5 psig, different PEEP other than 10 $mmH_2O$, different target shutoff pressure $P_{shutoff}$ and maximum output flow $V'_{aw-max}$ at the maximum nozzle pressure $P_n$, etc.

The controller 40 of the non-invasive ventilation system 10 (which may be a controller of an oxygen concentrator or ventilator as noted above) may be implemented with a programmable integrated circuit device such as a microcontroller or control processor. Broadly, the device may receive certain inputs, and based upon those inputs, may generate certain outputs. The specific operations that are performed on the inputs may be programmed as instructions that are executed by the control processor. In this regard, the device may include an arithmetic/logic unit (ALU), various registers, and input/output ports. External memory such as EEPROM (electrically erasable/programmable read only memory) may be connected to the device for permanent storage and retrieval of program instructions, and there may also be an internal random access memory (RAM). Computer programs for implementing any of the disclosed functionality of the controller 40 may reside on such non-transitory program storage media, as well as on removable non-transitory program storage media such as a semiconductor memory (e.g. IC card), for example, in the case of providing an update to an existing device. Examples of program instructions stored on a program storage medium or computer-readable medium may include, in addition to code executable by a processor, state information for execution by programmable circuitry such as a field-programmable gate arrays (FPGA) or programmable logic device (PLD).

In the above examples, a variable throat jet venturi 100 is implemented with a deformable throat body 120 whose cross-sectional area $A_t$ is selectively changed relative to a fixed cross-sectional area $A_n$ of a jet nozzle 110. However, it is also contemplated that the cross-sectional area $A_n$ of the jet nozzle 110 may itself be selectively decreased or increase instead of or in addition to the cross-sectional area $A_t$ of a deformable throat body 120. For example, the cross-sectional area $A_n$ of the jet nozzle 110 may be selectively changed by translating a tapered pin axially along the nozzle 110 or pressurizing an inflatable bladder similar to the plenum 140 described above. As another possibility, two jet nozzles 110 may be used, one for achieving PEEP at low nozzle flow $V'_n$ and the other for achieving desired $P_{shutoff}$-$V'_{aw-max}$ performance. Exemplary data of candidate jet nozzle diameters $D_t$ for use with the disclosed embodiments is shown in Table 7, below:

TABLE 7

| $P_n$ (psig) | $V'_n$ (slpm): | | | | | |
|---|---|---|---|---|---|---|
| | 0.94 mm 0.037" | 1.1 mm 0.043" | 1.2 mm 0.048" | 1.4 mm 0.055" | 1.5 mm 0.059" | 1.6 mm 0.063" |
| 1.0 | | 5.0 | 5.8 | 8.0 | 10.9 | 12.0 |
| 2.0 | | 8.3 | 8.9 | 12.3 | 14.9 | 16.8 |
| 4.0 | | 11.4 | 12.9 | 17.8 | 22.0 | 24.8 |
| 6.0 | | 13.9 | 15.8 | 21.3 | 26.7 | 30.3 |
| 8.0 | | 15.8 | 18.1 | 24.9 | 31.2 | |
| 10.0 | | 17.8 | 20.1 | 28.0 | | |
| 12.0 | | 19.8 | 22.0 | 30.3 | | |
| 14.0 | | 21.3 | 24.0 | | | |
| 16.0 | | 23.0 | 25.9 | | | |
| 18.0 | | 24.9 | 28.1 | | | |
| 20.0 | | 26.4 | 30.0 | | | |
| 22.0 | | 28.2 | | | | |
| 24.0 | | 29.8 | | | | |
| 26.0 | | 31.6 | | | | |
| 28.0 | | 32.9 | | | | |
| 30.0 | | 34.4 | | | | |

For ease of explanation, the above disclosure assumes that the variable throat jet venturi 100 has a single jet nozzle 110. As such, the cross-sectional area $A_n$ is described as corresponding to the diameter $D_n$ of the jet nozzle 110. However, the disclosure is not limited in this regard. For example, the variable throat jet venturi 100 may include a plurality of jet nozzles 110 arranged in a ring or other pattern. In this case, the cross-sectional area $A_n$ may refer to the total cross-sectional area of the plurality of jet nozzles 110 for purposes of evaluating the ratio $A_t/A_n$.

The above description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A variable throat jet venturi for delivering ventilation gas to a patient, the variable throat jet venturi comprising:
a jet nozzle;
a deformable throat body arranged to receive ventilation gas output by the jet nozzle and defining a gas inlet and a gas outlet; and
a housing containing the deformable throat body, the housing defining a pilot pressure port for pressurizing a plenum between an outer wall of the deformable throat body and an inner wall of the housing, the housing having a portion that flares outwardly away from the plenum and defines an entrainment opening which is arranged to draw ambient air directly therein, wherein the deformable throat body is arranged to receive the ventilation gas output by the jet nozzle through the entrainment opening of the housing.

2. The variable throat jet venturi of claim 1, wherein a distal tip of the jet nozzle is outside the entrainment opening.

3. The variable throat jet venturi of claim 1, wherein, with the plenum in a first pressurization state, the variable throat jet venturi achieves a shutoff pressure $P_{shutoff}$ at the gas outlet of at least 55 cmH$_2$O at a jet nozzle pressure $P_n$ of 10.5 psig and a jet nozzle flow $V'_n$ equal to or less than 30 slpm and, with the plenum in a second pressurization state, the variable throat jet venturi achieves a gas outlet pressure $P_{aw}$ of 10 cmH$_2$O at a jet nozzle flow $V'_n$ of less than 10 slpm.

4. The variable throat jet venturi of claim 3, wherein, with the plenum in the second pressurization state, the variable throat jet venturi achieves a gas outlet pressure $P_{aw}$ of 10 cmH$_2$O at a jet nozzle flow $V'_n$ of less than 5 slpm.

5. The variable throat jet venturi of claim 3, wherein, with the plenum in the first pressurization state, a ratio $A_t/A_n$ of a cross-sectional area of the deformable throat body to a cross-sectional area of the jet nozzle is between 20 and 30 and, with the plenum in the second pressurization state, the ratio $A_t/A_n$ is between 2.0 and 5.0.

6. A patient ventilation interface comprising:
the variable throat jet venturi of claim 1; and
a nasal coupler for fluidly coupling the gas outlet of the deformable throat body to a nostril of the patient.

7. The patient ventilation interface of claim 6, wherein the nasal coupler comprises a nasal pillow.

8. A non-invasive ventilation system comprising:
the patient ventilation interface of claim 6; and
a pilot pressure line fluidly coupled to the pilot pressure port.

9. The non-invasive ventilation system of claim 8, further comprising a controller programmed to energize the pilot pressure line to constrict the deformable throat body during an exhalation phase of positive end-expiratory pressure (PEEP) therapy.

10. The non-invasive ventilation system of claim 8, further comprising a multi-lumen tube having a ventilation gas lumen terminating in the jet nozzle and a pilot pressure lumen in fluid communication with the pilot pressure line.

11. A method of varying a ratio between a throat diameter and a jet nozzle diameter of a variable throat jet venturi for delivering ventilation gas to a patient, the method comprising:
providing a deformable throat body arranged to receive ventilation gas output by a jet nozzle, the deformable throat body defining a gas inlet and a gas outlet; and
pressurizing a plenum between an outer wall of the throat body and an inner wall of a housing containing the deformable throat body to constrict the deformable throat body, the housing having a portion that flares outwardly away from the plenum and defines an entrainment opening which is arranged to draw ambient air directly therein, wherein the deformable throat body is arranged to receive the ventilation gas output by the jet nozzle through the entrainment opening of the housing.

12. The method of claim 11, wherein said pressurizing the plenum includes energizing a pilot pressure line fluidly coupled to a pilot pressure port defined by the housing.

13. The method of claim 12, wherein said energizing is performed during an exhalation phase of positive end-expiratory pressure (PEEP) therapy.

14. The method of claim 11, wherein said pressurizing comprises pressurizing the plenum from a first pressurization state, in which the variable throat jet venturi achieves a shutoff pressure $P_{shutoff}$ at the gas outlet of at least 55 cmH$_2$O at a jet nozzle pressure $P_n$ of 10.5 psig and a jet nozzle flow $V'_n$ equal to or less than 30 slpm, to a second pressurization state, in which the variable throat jet venturi achieves a gas outlet pressure $P_{aw}$ of 10 cmH$_2$O at a jet nozzle flow $V'_n$ of less than 10 slpm.

15. The method of claim 14, wherein, with the plenum in the second pressurization state, the variable throat jet venturi achieves a gas outlet pressure $P_{aw}$ of 10 cmH$_2$O at a jet nozzle flow $V'_n$ of less than 5 slpm.

16. The method of claim 14, wherein, with the plenum in the first pressurization state, a ratio $A_t/A_n$ of a cross-sectional area of the deformable throat body to a cross-sectional area of the jet nozzle is between 20 and 30 and, with the plenum in the second pressurization state, the ratio $A_t/A_n$ is between 2.0 and 5.0.

17. A variable throat jet venturi for delivering ventilation gas to a patient, the variable throat jet venturi comprising:
a jet nozzle;
a deformable throat body arranged to receive ventilation gas output by the jet nozzle and defining a gas inlet and a gas outlet; and
a housing containing the deformable throat body, the housing defining a pilot pressure port for pressurizing a plenum between an outer wall of the deformable throat body and an inner wall of the housing, the housing having a portion that flares outwardly away from the plenum and defines an entrainment opening which is arranged to draw ambient air directly therein, wherein the deformable throat body is arranged to receive the ventilation gas output by the jet nozzle through the entrainment opening of the housing.

18. The variable throat jet venturi of claim 17, wherein, with the plenum in a first pressurization state, the variable throat jet venturi achieves a shutoff pressure $P_{shutoff}$ at the gas outlet of at least 55 cmH$_2$O at a jet nozzle pressure $P_n$ of 10.5 psig and a jet nozzle flow $V'_n$ equal to or less than 30 slpm and, with the plenum in a second pressurization state, the variable throat jet venturi achieves a gas outlet pressure $P_{aw}$ of 10 cmH$_2$O at a jet nozzle flow $V'_n$ of less than 10 slpm.

19. The variable throat jet venturi of claim 18, wherein, with the plenum in the second pressurization state, the variable throat jet venturi achieves a gas outlet pressure $P_{aw}$ of 10 cmH$_2$O at a jet nozzle flow $V'_n$ of less than 5 slpm.

20. The variable throat jet venturi of claim 18, wherein, with the plenum in the first pressurization state, a ratio $A_t/A_n$ of a cross-sectional area of the deformable throat body to a cross-sectional area of the jet nozzle is between 20 and 30 and, with the plenum in the second pressurization state, the ratio $A_t/A_n$ is between 2.0 and 5.0.

\* \* \* \* \*